United States Patent [19]

Del Rossi et al.

[11] Patent Number: 5,292,982

[45] Date of Patent: Mar. 8, 1994

[54] LIQUID ACID ALKYLATION CATALYST AND ISOPARAFFIN-OLEFIN ALKYLATION PROCESS

[75] Inventors: Kenneth J. Del Rossi, Woodbury, N.J.; Albin Huss, Jr., Chadds Ford, Pa.

[73] Assignee: Mobil Oil Corporation, Fairfax, Va.

[21] Appl. No.: 974,550

[22] Filed: Nov. 12, 1992

Related U.S. Application Data

[63] Continuation-in-part of Ser. No. 719,277, Jun. 21, 1991, Pat. No. 5,196,628, and a continuation-in-part of Ser. No. 761,567, Sep. 18, 1991, Pat. No. 5,202,518, and a continuation-in-part of Ser. No. 765,228, Sep. 25, 1991, abandoned, and a continuation-in-part of Ser. No. 719,276, Jun. 21, 1991, Pat. No. 5,220,096.

[51] Int. Cl.$^5$ ................................ C07C 2/62
[52] U.S. Cl. .................... 585/724; 585/723; 585/725; 585/730; 502/150; 502/170
[58] Field of Search ............... 585/722, 723, 724, 725, 585/730; 502/150, 170

[56] References Cited

U.S. PATENT DOCUMENTS

| | | | |
|---|---|---|---|
| 2,406,954 | 9/1946 | Linn | 260/683.4 |
| 2,615,908 | 10/1952 | McCaulay et al. | 585/724 |
| 3,531,546 | 9/1970 | Hervert | 585/724 |
| 3,778,489 | 12/1973 | Parker | 585/724 |
| 3,795,712 | 3/1974 | Torck | 585/724 |
| 3,856,764 | 12/1975 | Throckmorton | 585/724 |
| 4,636,488 | 1/1987 | Imai et al. | 585/724 |
| 4,938,935 | 7/1990 | Audeh et al. | 585/724 |
| 4,938,936 | 7/1990 | Yan | 585/724 |
| 4,985,220 | 1/1991 | Audeh et al. | 585/724 |
| 5,073,674 | 12/1991 | Olah | 585/725 |

*Primary Examiner*—Asok Pal
*Attorney, Agent, or Firm*—Alexander J. McKillop; Dennis P. Santini; Robert B. Furr, Jr.

[57] ABSTRACT

This invention provides an isoparaffin-olefin alkylation catalyst composition comprising hydrofluoric acid, an additive, and a superacid promoter. The additive is present in concentration sufficient to effect deactivation of the hydrofluoric acid for isoparaffin-olefin alkylation such that the catalytic properties of said admixture of the hydrofluoric acid and the additive, in the absence of superacid promoter are characterized by the conversion of a mixed isoparaffin-olefin stream to product containing more than about 0.1 weight percent of alkyl halide.

18 Claims, No Drawings

LIQUID ACID ALKYLATION CATALYST AND ISOPARAFFIN-OLEFIN ALKYLATION PROCESS

CROSS-REFERENCE TO RELATED APPLICATIONS

This is a continuation-in-part of allowed application Ser. No. 07/719,277, filed Jun. 21, 1991, now U.S. Pat. No. 5,196,628, allowed application, Ser. No. 07/761,567, filed Sep. 18, 1991, now U.S. Pat. No. 5,202,518, application Ser. No. 07/765,228, filed Sep. 25, 1991, now abandoned and application Ser. No. 07/719,276, filed Jun. 21, 1991, now U.S. Pat. No. 5,220,096. The entire text of each of these applications is incorporated herein by reference.

FIELD OF THE INVENTION

The present invention relates to the art of catalytic alkylation. The invention relates to a liquid alkylation catalyst and an isoparaffin-olefin alkylation process. Particularly, the invention provides a liquid alkylation catalyst complex which avoids many of the safety and environmental concerns associated with the handling, storage, and processing of concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. Acid strength is preferably maintained at 88 to 94 weight percent by the continuous addition of fresh acid and the continuous withdrawal of spent acid.

Hydrofluoric acid and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid complexes have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper complex compounds are listed from column 6, line 55 through column 8 at line 3. The method is said to be useful for purifying HF-containing vent gases from an industrial HF alkylation plant. See column 7, lines 10-24.

U.S. Pat. No. 3,531,546 to Hervert discloses a HF—$CO_2$ catalyst complex which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,636,488 discloses an anhydrous nonalcoholic alkylation catalyst comprising a mixture of a mineral acid and an ether in proportions of from about 50 to about 99 weight percent of mineral acid and from about 1 to about 50 weight percent of ether. Useful mineral acids include HF; see column 4 at lines 56-60.

Promoters such as alcohols, thiols, water, ethers, thioethers, sulfonic acids, and carboxylic acids are disclosed in combination with Bronsted acids such as HF, fluorosulfonic and trihalomethanesulfonic acids in U.S. Pat. No. 3,778,489 to Parker et al. The promoters are said to modify the activity of the Bronsted acids for alkylation.

U.S. Pat. No. 3,795,712 to Torck et al. teaches hydrocarbon alkylation in the presence of a sulfone and from $10^{-5}$ to 5 moles of hydrofluoric acid per liter of sulfone.

U.S. Pat. Nos. 4,025,577 and 4,094,924 to Siskin et al. teach isoparaffin-olefin alkylation catalysts comprising a hydrogen halide and a metal floride, and, optionally, a suitable diluent.

The preceding references describe catalyst complexes containing Bronsted acids which are useful as catalysts for various reactions. In view of the increasing safety and environmental concerns surrounding the cloud-forming tendency of hydrofluoric acid, providing an additive to mitigate Bronsted acid cloud formation while preserving the properties of the Bronsted acid for isoparaffin-olefin alkylation would be a major advance in the art.

SUMMARY OF THE INVENTION

In accordance with the present invention, it has been found that Bronsted acids such as HF and the halogenated sulfonic acids are effective as liquid isoparaffin-olefin alkylation catalysts under unusually dilute concentrations in the presence of both a superacid promoter and an additive selected from the group consisting of the compounds having the formula R'—(NO$_2$), wherein R' is an alkyl, aromatic, alkyl halide, or halide-substituted aromatic group having from about 1 to about 30 carbon atoms, carboxylic acids having the formula R"—COOH wherein R" is C$_6$H$_5$ or CF$_3$, and carbonates, (e.g., dimethylcarbonate, propylene carbonate tetrachloroethylene carbonate) having the formula ROC(O)OR or

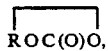

wherein R is an alkyl or an alkyl halide, or an aromatic or halogenated aromatic group having from about 1 to about 30 carbon atoms. The alkylation catalyst of the present invention, comprising a Bronsted acid diluted in the selected additive together with the superacid promoter provides commercially useful levels of catalytic activity for isoparaffin-olefin alkylation while minimizing both the stored inventory as well as the circulating Bronsted acid concentration within the commercial alkylation process unit.

Examples of useful superacid promoters include, but are not limited to BF$_3$, AlCl$_3$, AlBr$_3$, TaF$_5$, SbF$_5$, NbF$_5$, PF$_5$, BCl$_3$, TiF$_4$, CF$_3$SO$_3$H, and FSO$_3$H.

Both Bronsted and Lewis superacids are useful additives in the present invention. As used herein, the term "Bronsted superacid" includes the protic acids having acidity equal to or greater than that of 100% sulfuric acid. The term "Lewis superacid", as used herein, includes non-protic acids having Lewis acidity greater than or equal to that of aluminum trichloride. For a discussion of the Bronsted and Lewis acid/base concepts, see A. J. Gordan and R. A. Ford *The Chemist's Companion* 54 (1972).

The Bronsted acid catalyst component of the invention is diluted to minimize its cloud-forming tendency. Diluting the Bronsted acid to this extent, however, deactivates the Bronsted acid below the level of catalytic activity required for commercial isoparaffin-olefin alkylation. The method for determining the proportions of Bronsted acid, additive, and superacid promoter in the present invention varies slightly based upon the choice of Bronsted acid. If the Bronsted acid is HF, then the relative quantities of additive and Bronsted acid may be determined either by the formation of alkyl halides in the product (as described in greater detail below) or by alkylate quality (trimethylpentane formation). If the Bronsted acid is a halosulfonic acid, the relative quantities of additive and Bronsted acid are determined by alkylate quality because mixtures of the additives of the invention and Bronsted acids have not been observed to form alkyl halides as a result of diluting the Bronsted acid with the selected additives of the invention.

The invention provides, in a first aspect, a catalyst composition for alkylation of an isoparaffin with an olefin comprising:

(a) hydrofluoric acid;

(b) an additive in admixture with said hydrofluoric acid, said additive selected from the group consisting of the compounds having the formula R'—(NO$_2$), wherein R' is an alkyl, aromatic, alkyl halide, or halide-substituted aromatic group having from about 1 to about 30 carbon atoms, the compounds having the formula R"—COOH wherein R" is C$_6$H$_5$ or CF$_3$ and the compounds having the formula ROC(O)OR or

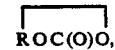

wherein R is an alkyl or an alkyl halide, or an aromatic or halogenated aromatic group having from about 1 to about 30 carbon atoms, wherein said additive is present in a quantity sufficient to effect deactivation of said hydrofluoric acid for isoparaffin-olefin alkylation such that the catalytic properties of said admixture of said hydrofluoric acid and said additive, in the absence of superacid promoter are characterized by the conversion of a mixed isoparaffin-olefin stream to product containing more than about 0.1 weight percent of alkyl halide; and (c) a superacid promoter in concentration sufficient such that contacting said catalyst composition comprising said hydrofluoric acid, said additive, and said superacid promoter with a mixed isobutane/2-butene feedstream in an isobutane/2-butene molar ratio of more than about 2:1 under alkylation conversion conditions yields a product containing at least 50 weight percent of the trimethylpentanes obtained by contacting said isobutane/2-butene feedstream with concentrated HF under said alkylation conversion conditions.

The invention further provides, in a second aspect, a catalyst composition for alkylation of an isoparaffin with an olefin comprising:

(a) a halogenated sulfonic acid;

(b) an additive in admixture with said halogenated sulfonic acid, said additive selected from the group consisting of the compounds having the formula R'—(NO$_2$), wherein R' is an alkyl, aromatic, alkyl halide, or halide-substituted aromatic group having from about 1 to about 30 carbon atoms, the compounds having the formula R"—COOH wherein R" is C$_6$H$_5$ or CF$_3$ and the compounds having the formula ROC(O)OR or

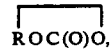

wherein R is an alkyl or an alkyl halide, or an aromatic or halogenated aromatic group having from about 1 to about 30 carbon atoms, wherein said additive is present in a quantity sufficient to effect deactivation of said halogenated sulfonic acid for isoparaffin-olefin alkylation such that the catalytic properties of said admixture of said halogenated sulfonic acid and said additive, in the absence of superacid promoter are characterized by the conversion of a mixed isobutane/2-butene feedstream in an isobutane/2-butene molar ratio of more than about 2:1 under alkylation conversion conditions to product containing less than about 50 weight percent of the trimethylpentanes obtained by contacting said mixed isobutane/2-butene stream with neat halogenated sulfonic acid under said alkylation conversion conditions; and (c) a superacid promoter in concentration sufficient such that contacting said catalyst composition comprising said halogenated sulfonic acid, said additive, and said superacid promoter with a mixed isobutane/2-butene feedstream in an isobutane/2-butene molar ratio of more than about 2:1 under alkylation conversion conditions yields a product containing at least 50 weight percent of the trimethylpentanes obtained by contacting said isobutane/2-butene feedstream with concentrated halogenated sulfonic acid under said alkylation conversion conditions.

The invention further provides a process for alkylating an isoparaffin with an olefin comprising contacting at least one isoparaffin and at least one olefin with a catalyst composition of the invention under alkylation conversion conditions.

DETAILED DESCRIPTION

The invention provides a liquid isoparaffin-olefin alkylation catalyst composition which provides commercially useful levels of isoparaffin-olefin alkylation activity while avoiding safety and environmental concerns attendant to the storage, transfer, and processing of concentrated HF. As used herein, the terms "concentrated HF" and "concentrated hydrofluoric acid" refer to hydrofluoric acid solutions containing more than about 96 weight percent HF.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, pentene, hexene, heptene, and octene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Additive Donor Number

The term "donicity" describes the propensity of a solvent to donate electron pairs to acceptor solutes. The term "Donor Number" (DN) as used herein is a measure of donicity, and is defined as the negative of the enthalpy change, measured in Kcal-mol$^{-1}$, for the reaction of the additive with SbCl$_5$ to form a 1:1 adduct, where both reactants are in dilute solution in 1,2-dichloroethane (DCE). For a discussion of donicity and Donor Numbers, see Y. Marcus, "The Effectivity of Solvents as Electron Pair Donors", 13 *Journal of Solution Chemistry* 599 (1984). The Table below, reports donor numbers listed in the Marcus article for various solvents.

Additives useful in the present invention include nitroalkanes, (e.g., nitromethane and 1-nitropropane), carbonates, (e.g., dimethylcarbonate, propylene carbonate tetrachloroethylene carbonate) having the formula ROC(O)OR or

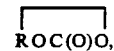

wherein R is an alkyl or an alkyl halide, or an aromatic or halogenated aromatic group having from about 1 to about 30 carbon atoms, of which propylene carbonate

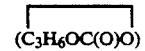

is a particularly preferred carbonate with tetrachloroethylene carbonate as an example of a suitable alkyl halide-containing carbonate additive. Useful additives also include perhalogenated alkanes (e.g., perfluorodecalin), halogenated alcohols (e.g., 2,2,2-trifluoroethanol), sulfonic acids having the formula R—SO$_3$H, wherein R is an aromatic group or a linear, branched, cyclic, or polycyclic alkyl group containing from about 1 to about 30 carbon atoms (e.g., methanesulfonic acid, ethanesulfonic acid, propanesulfonic acid, hexanesulfonic acid, cyclohexanesulfonic acid, adamantanesulfonic acid, benzenesulfonic acid and other branched, straight chain, monocyclic, and polycyclic aromatic sulfonic acids). Additional useful additives include the sulfones (e.g., a sulfone having the formula R—SO$_2$—R' wherein R and R' are the same or different alkyl or halogenated alkyl groups, of which one example comprises sulfolane), as well as acetyl chloride, benzoyl fluoride, methyl propionate, sulfuryl chloride, and sulfuryl chloride fluoride.

Donor Numbers for some of these useful additives are listed below in Table 1.

TABLE 1

| Additive | DN | Additive | DN |
| --- | --- | --- | --- |
| 1,2-dichloroethane | (0) | Methyl-t-butylketone | 17.0 |
| Acetyl Chloride | 0.7 | Diethyl Ether | 19.2 |
| Benzoyl Chloride | 2.3 | Tetrahydrofuran | 20.0 |
| Sulfuryl Chloride | 0.1 | Triethylamine | 30.5 |
| Thionyl Chloride | 0.4 | Pyridine | 33.1 |
| Selenoyl Chloride | 12.2 | Acetonitrile | 14.1 |
| Phosphoryl Chloride | 11.7 | Propanonitrile | 16.1 |
| Tetrachloroethylene Carbonate | 0.8 | Butanonitrile | 16.6 |
|  |  | Isobutanonitrile | 15.4 |
| Dichloroethylene Carbonate | 2.7 | Benzyl Cyanide | 15.1 |
|  |  | Benzonitrile | 11.9 |
| Nitromethane | 2.7 | N,N-Dimethylformamide | 26.6 |
| Nitrobenzene | 4.4 | N,N-Diethylformamide | 30.9 |
| Acetic Anhydride | 10.5 | N,N-Dimethylacetamide | 27.8 |
| Methyl Acetate | 16.4 | N,N-Diethylacetamide | 32.2 |
| Ethyl Acetate | 17.1 | Tetramethyl Urea | 29.6 |
| 2-Propyl Acetate | 17.5 | Hexamethyl Phosphoric Triamide | 38.8 |
| Ethyl Propanoate | 17.1 |  |  |
| Ethyl Butanoate | 16.8 | Ethylene Sulfite | 15.3 |
| Ethyl Isobutanoate | 16.4 | Dimethylsulfoxide | 29.8 |
| Ethyl t-Pentanoate | 12.9 | Tetramethylene Sulfone | 14.8 |
| Diethylcarbonate | 16.0 | Phenyldifluorophosphine Oxide | 16.4 |
| Ethylene Carbonate | 16.4 |  |  |
| 1,2-Propylene Carbonate | 15.1 | Phenyldichlorophosphine Oxide | 18.5 |
| Acetone | 17.0 | Diphonylchlorophosphine Oxide | 22.4 |
| 2-Butanone | 17.4 |  |  |
| Methylisopropyl- | 17.1 | Trimethyl Phosphate | 23.0 |

TABLE 1-continued

| Additive | DN | Additive | DN |
|---|---|---|---|
| ketone | | Tri-n-butyl Phosphate | 23.7 |

Thus additives useful in the present invention are characterized by Donor Numbers of from about 1 to about 40, preferably less than about 30, more preferably less than about 16. While additives characterized by lower Donor Numbers are preferred, it is to be understood that solvents having higher Donor Numbers within the range of about 1 to about 40 are also useful. Examples of such useful additives include amines such as pyridine and ammonia compounds as well as alcohols such as methanol and ethanol. The most preferred additives include those selected from the group consisting of the compounds having the formula R'—(NO$_2$), wherein R' is an alkyl, aromatic, alkyl halide, or halide-substituted aromatic group having from about 1 to about 30 carbon atoms, the compounds having the formula R"—COOH wherein R" is C$_6$H$_5$ or CF$_3$, and carbonates having the formula ROC(O)OR or

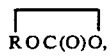

wherein R is an alkyl or an alkyl halide, or an aromatic halogenated aromatic group having from about 1 to about 30 carbon atoms.

The catalyst composition of the invention typically contains from about 10 to about 90 weight percent of a Bronsted acid selected from the group consisting of hydrofluoric acid and the halosulfonic acids, preferably from about 20 to about 80 weight percent of the Bronsted acid, and more preferably from about 40 to about 60 weight percent of the Bronsted acid. Additive content in the catalyst composition of the invention typically ranges from about 10 to about 90 weight percent, preferably from about 20 to about 80 weight percent, and more preferably from about 40 to about 60 weight percent of additive. Useful promoter concentrations vary with the relative concentrations of Bronsted acid and additive, with the superacid promoter typically being present in molar ratios of superacid promoter:Bronsted acid from about 1:200 to about 1:1, preferably from about 1:100 to about 1:2.

The purpose of formulating a liquid alkylation catalyst containing both a Bronsted acid as well as a superacid promoter in accordance with the present invention is (as noted above) to mitigate the cloud forming tendency of the Bronsted acid while preserving isoparaffin-olefin alkylation activity. Determining the extent to which a selected Bronsted acid must be diluted with a selected additive within the concentration ranges disclosed above to achieve the desired reduction in vapor pressure (and cloud forming tendency) requires only a minor amount of trial and error.

Process Conditions

The catalyst composition of the present invention may be readily substituted for the concentrated hydrofluoric acid catalyst in an existing hydrofluoric acid alkylation process without substantial equipment modifications. Accordingly, the conversion conditions for the process of the present invention resemble those of typical commercial hydrofluoric acid alkylation processes.

The present alkylation process is suitably conducted at temperatures of from about 10° to about 500° C., preferably from about 10° to about 200° C., and more preferably from about 20° C. to about 60° C. Pressure is maintained to ensure a liquid phase in the alkylation reaction zone. Pressures typically range from about 20 to about 1,200 psig preferably from about 50 to about 500 psig. Olefin feed rates generally range from about 0.01 to about 10 WHSV and more preferably from about 0.05 to about 5 hr$^{-1}$ WHSV. The mixed isoparaffin-olefin reactants may be contacted with the catalyst composition of the invention in any suitable reaction vessel, examples of which include stirred-tank reactors as well as riser-type reactors. Contact time for the mixed isoparaffin-olefin feed and the catalyst composition of the invention typically are within the range of from about 0.1 second to about 100 minutes, and more preferably from about 10 seconds to about 20 minutes.

The superacid promoter, the Bronsted acid, and the additive components of the alkylation catalyst composition may be added by injection directly into the alkylation process unit, or may be mixed with the hydrocarbon charge, or may be mixed with the fresh and/or circulating catalyst, or with a stream of mixed acid/additive catalyst. Downstream from the alkylation reaction zone, the catalyst mixture is preferably separated from the alkylate product stream, mixed with fresh and/or circulating catalyst, and recycled to the alkylation reaction zone. The particular separation technique selected, however, depends upon the characteristics of the catalyst, and in particular the combination of Bronsted acid, additive, and superacid promoter selected in accordance with the present invention.

EXAMPLE 1

The alkylation performance of HF (99+%, Matheson) was determined for comparison with ternary HF/additive/promoter mixtures. HF (40 grams) was condensed into a clean, dry 1,000 cc autoclave. The autoclave was warmed to room temperature (71° F.). Isobutane (100 grams, Matheson) was added, the autoclave was pressurized to 100 psig and stirred at 1,500 rpm. A pre-mixed 10/1 wt/wt isobutane/2-butene feed (Matheson) was then introduced at 250 cc/hr. A 10°-12° F. temperature rise was observed during feed addition. After two hours, feed addition was halted and a 300 cc liquid sample was obtained. The liquid sample was depressured through an ice cooled trap (filled with 50 cc of water) which was connected to a gas sampling bomb and wet test meter. Liquid alkylate and gas samples were analyzed with a Varian 6000 gas chromatograph equipped with a 60 meter DB-1 capillary column.

EXAMPLE 2

1-Nitropropane (60 grams, Aldrich Chemical Co.) was loaded into a clean, dry 1,000 cc autoclave under a nitrogen atmosphere. The autoclave was sealed, and cooled with liquid nitrogen. The autoclave was evacuated and 40 grams of anhydrous HF (Matheson) were condensed into the autoclave. The HF/1-nitropropane mixture was warmed to room temperature (71° F.). Isobutane (100 grams, Matheson) was added to the mixture, the autoclave was pressurized to 100 psig and stirred at 1,500 rpm. A pre-mixed 10/1 wt/wt isobutane/2-butene feed (Matheson) was then introduced at 250 cc/hr. A 2°-3° F. temperature rise was observed during feed addition. After two hours, feed addition was halted and a 300 cc liquid sample was obtained. The liquid sample was depressured through an ice cooled trap (filled with 50 cc of water) which was connected to a gas sampling bomb and wet test meter. A gas product was collected and analyzed with a Varian 6000 gas chromatograph equipped with a 60 meter DB-1 capillary column.

The GC analysis showed only butyl fluoride, $C_4H_9F$, with no detectable $C_5+$ hydrocarbons.

EXAMPLE 3

The identical procedure as in Example 2 was performed except 5 grams of fluorosulfonic acid (Aldrich Chemical Co.) were added to the HF/1-nitropropane mixture. A 10°-12° F. temperature rise was observed during feed addition, and a water-white liquid was obtained. The total product composition is compared with the product from Example 1, the HF base case run, in Table 2.

The results show that addition of a superacid promoter, such as fluorosulfonic acid, to an inactive HF/additive mixture can restore alkylation performance to levels near that of concentrated HF.

TABLE 2

|  | Ex. 1 | Ex. 2 | Ex. 3 |
|---|---|---|---|
| Catalyst Mixture |  |  |  |
| HF (gm) | 40 | 40 | 40 |
| 1-Nitropropane (gm) | 0 | 60 | 60 |
| Fluorosulfonic Acid (gm) | 0 | 0 | 5 |
| Alkylate Composition, wt % |  |  |  |
| $C_5$—$C_7$ | 5.5 | (1) | 2.0 |
| $C_8$ | 88.1 |  | 89.7 |
| $C_9+$ | 6.4 |  | 8.3 |
| Trimethylpentanes, wt % | 79.4 |  | 77.2 |
| TMP/DMH | 9.2 |  | 6.2 |
| Olefin Conversion, % | 99.9 |  | 99.7 |

(1) Only butyl fluoride produced, no detectable $C_5+$ alkylate product.

Changes and modifications in the specifically described embodiments can be carried out without departing from the scope of the invention which is intended to be limited only by the scope of the appended claims.

What is claimed is:

1. A catalyst composition for aklylation of an isoparaffin with an olefin comprising:
   (a) hydrofluoric acid;
   (b) an additive in admixture with said hydrofluoric acid, said additive selected from the group consisting of the compounds having the formula R'—(-NO$_2$), wherein R' is an alkyl, aromatic, alkyl halide, or halide-substituted aromatic group having from about 1 to about 30 carbon atoms, the compounds having the formula R"—COOH wherein R" is $C_6H_5$ or $CF_3$, and the compounds having the formula ROC(O)OR or

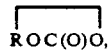

wherein R is an alkyl or an alkyl halide, or an aromatic or halogenated aromatic group having from about 1 to about 30 carbon atoms, wherein said additive is present in a quantity sufficient to effect deactivation of said hydrofluoric acid for isoparaffin-olefin alkylation such that the catalytic properties of said admixture of said hydrofluoric acid and said additive, in the absence of superacid promoter are characterized by the conversion of a mixed isoparaffin-olefin stream to product containing more than about 0.1 weight percent of alkyl halide; and
   (c) a superacid promoter selected from the group consisting of BF$_3$, AlCl$_3$, AlBr$_3$, TaF$_5$, SbF$_5$, NbF$_5$, PF$_5$, BCl$_3$, TiF$_4$, CF$_3$SO$_3$H, and FSO$_3$H in concentration sufficient such that contacting said catalyst composition comprising said hydrofluoric acid, said additive, and said superacid promoter with a mixed isobutane/2-butene feedstream in an isobutane/2-butene molar ratio of more than about 2:1 under alkylation conversion conditions yields a product containing at least 50 percent of the trimethylpentanes obtained by contacting said isobutane/2-butene feedstream with concentrated HF under said alkylation conversion conditions.

2. The catalyst composition of claim 1 comprising from about 10 to about 90 weight percent of said additive.

3. The catalyst composition of claim 2 comprising from about 20 to about 80 weight percent of said additive.

4. The catalyst composition of claim 1 wherein said additive is a nitroalkane or an alkyl carbonate.

5. A process for alkylating an isoparaffin with an olefin comprising effecting reaction of isoparaffin and olefin with an alkylation catalyst composition comprising:
   (a) hydrofluoric acid;
   (b) an additive in admixture with said hydrofluoric acid, said additive selected from the group consisting of the compounds having the formula R'—(-NO$_2$), wherein R' is an alkyl, aromatic, alkyl halide, or halide-substituted aromatic group having from about 1 to about 30 carbon atoms, the compounds having the formula R"—COOH wherein R" is $C_6H_5$ or $CF_3$, and the compounds having the formula ROC(O)OR or

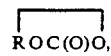

wherein R is an alkyl or an alkyl halide, or an aromatic or halogenated aromatic group having from about 1 to about 30 carbon atoms, wherein said additive is present in a quantity sufficient to effect deactivation of said hydrofluoric acid for isoparaffin-olefin alkylation such that the catalytic properties of said admixture of said hydrofluoric acid and said additive, in the absence of superacid promoter are characterized by the conversion of a mixed isoparaffin-olefin stream to product containing more than about 0.1 weight percent of alkyl halide; and
   (c) a superacid promoter selected from the group consisting of BF$_3$, AlCl$_3$, AlBr$_3$, TaF$_5$, SbF$_5$, NbF$_5$, PF$_5$, BCl$_3$, TiF$_4$, CF$_3$SO$_3$H, and FSO$_3$H in concentration sufficient such that contacting said catalyst composition comprising said hydrofluoric acid, said additive, and said superacid promoter with a mixed isobutane/2-butene feedstream in an isobutane/2-butene molar ratio of more than about 2:1 under alkylation conversion conditions yields a product containing at least 50 percent of the trimethylpentanes obtained by contacting said isobutane/2-butene feedstream with concentrated HF under said alkylation conversion conditions.

6. The process of claim 5 wherein said additive is a nitroalkane or an alkyl carbonate.

7. The process of claim 5 wherein said additive comprises from about 10 to about 90 weight percent of said catalyst composition.

8. The process of claim 7 wherein said additive comprises from about 20 to about 80 weight percent of said catalyst composition.

9. The process of claim 5 further comprising charging said isoparaffin and said olefin to a riser reactor containing said catalyst composition.

10. A process for alkylating an isoparaffin with an olefin comprising effecting reaction of isoparaffin and olefin with an alkylation catalyst composition comprising:
(a) at least one Bronsted acid selected from the group consisting of hydrofluoric acid and the halogenated sulfonic acid;
(b) an additive in admixture with said Bronsted acid, said additive selected from the group consisting of the compounds having the formula R'—(NO$_2$), wherein R' is an alkyl, aromatic, alkyl halide, or halide-substituted aromatic group having from about 1 to about 30 carbon atoms, the compounds having the formula R"—COOH wherein R" is C$_6$H$_5$ or CF$_3$ and compounds having the formula ROC(O)OR or

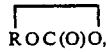

wherein R is an alkyl or an alkyl halide, or an aromatic or halogenated aromatic group having from about 1 to about 30 carbon atoms, wherein said additive is present in a quantity sufficient to effect deactivation of said Bronsted acid for isoparaffin-olefin alkylation such that the catalytic properties of said admixture of said Bronsted acid and said additive, in the absence of superacid promoter are characterized by the conversion of a mixed isobutane/2-butene feedstream in an isobutane/2-butene molar ratio of more than about 2:1 under alkylation conversion conditions to product containing less than about 50 weight percent of the trimethylpentanes obtained by contacting said mixed isobutane/2-butene stream with said Bronsted acid under said alkylation conversion conditions; and
(c) a superacid promoter in concentration sufficient such that contacting said liquid alkylation catalyst composition with a mixed isobutane/2-butene feedstream in an isobutane/2-butene molar ratio of more than about 2:1 under alkylation conversion conditions yields a product containing at least 50 weight percent of the trimethylpentanes obtained by contacting said isobutane/2-butene feedstream with said Bronsted acid under said alkylation conversion conditions.

11. The process of claim 10 wherein said additive is a nitroalkane.

12. The process of claim 10 wherein said additive comprises from about 10 to about 90 weight percent of said catalyst composition.

13. The process of claim 12 wherein said additive comprises from about 20 to about 80 weight percent of said catalyst composition.

14. The process of claim 10 further comprising charging said isoparaffin and said olefin to a riser reactor containing said catalyst composition.

15. A process for alkylating an isoparaffin with an olefin comprising effecting reaction of isoparaffin and olefin with an alkylation catalyst composition which composition consists essentially of:
(a) hydrofluoric acid;
(b) an additive in admixture with said hydrofluoric acid, said additive selected from the group consisting of nitroalkanes and alkyl carbonates, wherein said additive is present in a quantity sufficient to effect deactivation of said Bronsted acid for isoparaffin-olefin alkylation such that the catalytic properties of said admixture of said hydrofluoric acid and said additive, in the absence of superacid promoter are characterized by the conversion of a mixed isoparaffin-olefin stream to product containing more than about 0.1 weight percent of alkyl halide; and
(c) a superacid promoter selected from the group consisting of BF$_3$, AlCl$_3$, AlBr$_3$, TaF$_5$, SbF$_5$, NbF$_5$, PF$_5$, BCl$_3$, TiF$_4$, CF$_3$SO$_3$H, and FSO$_3$H in concentration sufficient such that contacting said catalyst composition comprising said hydrofluoric acid, said additive, and said superacid promoter with a mixed isobutane/2-butene feedstream in an isobutane/2-butene molar ratio of more than about 2:1 under alkylation conversion conditions yields a product containing at least 50 weight percent of the trimethylpentanes obtained by contacting said isobutane/2-butene feedstream with concentrated HF under said alkylation conversion conditions.

16. The process of claim 15 wherein said additive is a nitroalkane or an alkyl carbonate.

17. The process of claim 15 wherein said additive comprises from about 20 to about 80 weight percent of said catalyst composition.

18. A catalyst composition for alkylation of an isoparaffin with an olefin, said catalyst composition consisting essentially of:
(a) hydrofluoric acid;
(b) an additive in admixture with said hydrofluoric acid, said additive selected from the group consisting of nitroalkanes and alkyl carbonates, wherein said additive is present in a quantity sufficient to effect deactivation of said hydrofluoric acid for isoparaffin-olefin alkylation such that the catalytic properties of said admixture of said hydrofluoric acid and said additive, in the absence of superacid promoter are characterized by the conversion of a mixed isoparaffin-olefin stream to product containing more than about 0.1 weight percent of alkyl halide; and
(c) a superacid promoter selected from the group consisting of BF$_3$, AlCl$_3$, AlBr$_3$, TaF$_5$, SbF$_5$, NbF$_5$, PF$_5$, BCl$_3$, TiF$_4$, CF$_3$SO$_3$H, and FSO$_3$H in concentration sufficient such that contacting said catalyst composition comprising said hydrofluoric acid, said additive, and said superacid promoter with a mixed isobutane/2-butene feedstream in an isobutane/2-butene molar ratio of more than about 2:1 under alkylation conversion conditions yields a product containing at least 50 percent of the trimethylpentanes obtained by contacting said isobutane/2-butene feedstream with concentrated HF under said alkylation conversion conditions.

* * * * *